United States Patent [19]

Baumann

[11] 4,267,249
[45] May 12, 1981

[54] BENZENE DIAZONIUM SALTS AND DIAZOTYPE MATERIAL UTILIZING SAME

[75] Inventor: Niklaus Baumann, Marly, Switzerland

[73] Assignee: Aerni-Leuch AG, Kanton Bern, Switzerland

[21] Appl. No.: 68,565

[22] Filed: Aug. 22, 1979

[30] Foreign Application Priority Data

Aug. 22, 1978 [CH] Switzerland ............... 8923/78

[51] Int. Cl.³ ............... G03C 1/54; C07C 113/04
[52] U.S. Cl. .................. 430/187; 430/149; 430/186; 260/141
[58] Field of Search ............... 430/186, 187, 149; 260/141 R, 141 H

[56] References Cited

U.S. PATENT DOCUMENTS

| | | | |
|---|---|---|---|
| 3,281,245 | 10/1966 | Werner et al. | 430/186 |
| 3,311,475 | 3/1967 | Van Loon et al. | 430/187 |
| 3,338,713 | 8/1967 | Hendrickx et al. | 430/187 |
| 3,397,058 | 8/1968 | Van Loon et al. | 260/141 R |
| 3,397,985 | 8/1968 | Hendrickx | 430/187 |
| 3,407,066 | 10/1968 | Mustacchi et al. | 430/187 |
| 3,520,692 | 7/1970 | Knoester et al. | 260/141 R |
| 3,547,637 | 12/1970 | Scheler et al. | 430/186 |
| 3,868,255 | 2/1975 | Garnish et al. | 430/187 |

FOREIGN PATENT DOCUMENTS

| | | |
|---|---|---|
| 1476460 | 2/1967 | France. |
| 1543870 | 9/1968 | France. |
| 7128543 | 7/1975 | France. |
| 51536 | 11/1941 | Netherlands. |
| 386841 | 1/1965 | Switzerland. |

Primary Examiner—Charles L. Bowers
Attorney, Agent, or Firm—Oblon, Fisher, Spivak, McClelland & Maier

[57] ABSTRACT

Benzene diazonium compounds of the general formula

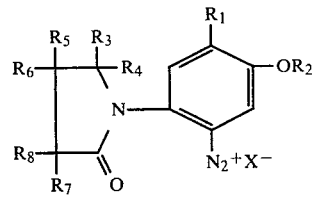

wherein $R_1$ is alkylamino, dialkylamino, cycloalkylamino, dicycloalkylamino, cycloalkylalkylamino, aralkylamino, diaralkylamino, alkylaralkylamino, cycloalkylaralkylamino, arylamino, diarylamino, alkylarylamino, cycloalkylarylamino, acoylamino, acoylalkylamino, acoylcycloalkylamino, acoylaralkylamino, acoylarylamino, aroylamino, aroylalkylamino, aroylcycloalkylamino, aroylaralkylamino, aroylarylamino, morpholino, piperidino, triazinyl, alkylthio, hydroxyalkylthio, cycloalkylthio, aralkylthio, or arylthio; $R_2$ is alkyl, aralkyl, aryl, or alkoxyalkyl; $R_3$, $R_4$, $R_5$, $R_6$, $R_7$ and $R_8$ may be the same or different and are hydrogen, alkyl, cycloalkyl, aralkyl, aryl, or halogen, at least one of the substituents $R_3$ to $R_8$ not being hydrogen; and X is an anion. Salts of the foregoing compounds are utilized in diazotype materials having improved water resistance and speed of development without impairment of other characteristics such as light sensitivity.

6 Claims, No Drawings

BENZENE DIAZONIUM SALTS AND DIAZOTYPE MATERIAL UTILIZING SAME

This invention relates to benzene diazonium salts suitable for the production of diazotype material, particularly one-component diazotype material, having improved water resistance and adequate speed of development.

In practice, the salts of 4-arylmercapto-2,5-dialkoxy-1-diazobenzene, particularly 1-diazo-2,5-dimethoxy-4-p-tolylmercaptobenzene, have proved satisfactory for one-component materials. These compounds are mentioned in Fiat Final Report 813, pages 138 and 137, and in Dutch Pat. No. 51,536. Compounds of this type, used with conventional phloroglucinol developers, yield black azo dyes having good light fastness and present no problems as regards secondary color densities. However, because of moderate light sensitivity and slow coupling activity in the presence of the usual weakly acid developers, the aforementioned compounds remain limited to use in slow-copying papers. A substantial improvement in the light sensitivity is achieved with the 2-chloro-5-p-chlorophenoxy-4-N,N-dialkylamino-1-diazobenzene compounds described in Swiss Pat. No. 386,841. These compounds nevertheless exhibit slow coupling activity and are therefore limited in their application. This drawback is one of the reasons why these compounds are not suitable for use in transparent diazotype materials since owing to the higher diazonium salt content with respect to opaque materials, complete development does not take place in one operation with acid developers. An appreciable improvement in this respect is shown by diazonium salts of the 4-arylmercapto-1-diazo-5-methoxy-1-N-methyl-N-alkoxycarbonylamino-benzene type, described in Swiss Pat. No. 448,734, and of the 4-aryl-mercapto-1-diazo-5-methoxy-2-pyrrolid-(2)-one-(1)-yl-benzene type disclosed in Swiss Pat. No. 451,701, or compounds of the 4-alkyl-mercapto-1-diazo-5-methoxy-2-pyrrolid-(2)-one-(1)-yl-benzene type of Swiss Pat. No. 448,734 and German Pat. No. 1,472,798, and compounds such as 1-diazo-4-dimethylamino-5-methoxy-2-pyrrolid-2-one-1-yl-benzene of U.S. Pat. No. 3,868,255.

Experience has shown that the foregoing compounds still do not represent the optimum for use in transparent materials as regards coupling speed, light fastness, and wet fastness, especially when used with coated tracing papers and films. All coatings used in practice, e.g., based on partially hydrolyzed cellulose esters or other polymers having hydrophilic groups, such as copolymers of the acrylic acid type, exhibit a partially hydrophobic character. The speed of penetration of the aqueous developer is greatly influenced thereby. As a result, insufficient color density appears in the unexposed portions of the copy, especially with high-speed copy-developing machines, and this leads to a loss of content in repeat copies.

It is an object of this invention to provide new diazonium salts which do not exhibit the shortcomings of too slow development, and yet do not manifest such negative properties as insufficient light sensitivity, secondary color densities and poor light fastness of the azo dyes formed.

Another object of this invention is to provide diazonium salts having improved resistance against aqueous developers and improved wet fastness of the azo dyes formed after development as compared with the types of compounds disclosed in Swiss Pat. Nos. 448,734 and 451,701 and in German Pat. No. 1,472,798. These properties result in significantly less bleeding, thus ensuring optimum reproduction of lines, Furthermore, the good wet fastness results in an improvement of offset plates produced on this basis.

The novel benzene diazonium compounds according to the present invention are of the formula

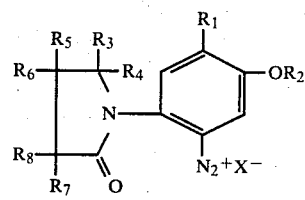

wherein $R_1$ is alkylamino, dialkylamino, cycloalkylamino, dicycloalkylamino, cycloalkylalkylamino, aralkylamino, diaralkylamino, alkylaralkylamino, cycloalkylaralkylamino, arylamino, diarylamino, alkylarylamino, cycloalkylarylamino, acoylamino, acoylalkylamino, acoylcycloalkylamino, acoylaralkylamino, acoylarylamino, aroylamino, aroylalkylamino, aroylcycloalkylamino, aroylaralkylamino, aroylarylamino, morpholino, piperidino, triazinyl, alkylthio, hydroxyalkylthio, cycloalkylthio, aralkylthio, or arylthio; $R_2$ is alkyl, aralkyl, aryl, or alkoxyalkyl; $R_3$, $R_4$, $R_5$, $R_6$, $R_7$ and $R_8$ may be the same or different and are hydrogen, alkyl, cycloalkyl, aralkyl, aryl, or halogen, at least one of the substituents $R_3$ to $R_8$ not being hydrogen; and X is an anion.

Preferred compounds of formula I are those in which $R_1$ is arylthio, alkylthio, or aralkylthio; $R_2$ is methyl, ethyl, alkoxyalkyl having 1 or 2 carbon atoms each in the alkyl and alkoxy radicals, or substituted or unsubstituted phenyl; $R_3$ is methyl; $R_4$ to $R_8$ are hydrogen; and X is an organic or inorganic anion.

Any organic or inorganic salts enter into consideration as salts of the compounds of formula I, e.g., simple salts such as the chloride, sulfate, tetrafluoroborate, hexafluorophosphate, or hexafluoroarsenate, or double salts such as the chlorides of zinc, iron, cobalt, antimony, or tin; the zinc chloride double salt being preferred. As organic salts, those having organic sulfonates, e.g., 1,3,6-trisulfonaphthalene, 1,5-disulfonaphthalene, or 1,6-disulfonaphthalene may be mentioned.

Particularly preferred compounds of formula I are those in which $R_1$ is p-methylphenylthio, phenylthio, benzylthio, or butylthio; $R_2$ is methyl, ethyl, methoxyethyl, or p-chlorophenyl; $R_3$ is methyl, $R_4$ to $R_8$ are hydrogen, as zinc chloride double salts.

The compounds according to the invention are preferably synthesized starting from 3,4-dichloro-nitrobenzene. In the first step of the reaction, the nucleophilic substitution of an alkoxy or aryloxy group for the chlorine atom in the 4 position takes place. Next, the nitro group is reduced to the corresponding aniline and thereafter condensed with a substituted butyrollactone, water being split off to the aniline, to form an N-substituted aromatic lactam. The latter can be nitrated extraordinarily well and in all cases in the para position to the chlorine atom of the aromatic ring.

Replacement of the chlorine atom takes place through nucleophilic substitution by means of mercaptans or amines. These reactions proceed under relatively mild conditions and yield very uniform products.

The subsequent reduction of the nitro group to the amine is easily carried out catalytically or by conventional methods. In particular, the substituted butyrolactam ring proves to be extraordinarily resistant to hydrolysis or hydrogenolysis as compared with the unsubstituted butyrolactam ring or with an open-chain —N—C=O linkage. Hence the compounds according to this invention also differ advantageously from similar prior art compounds as regards their preparation.

The amine is converted into the diazonium salt in the usual manner. If it is desired to obtain 5-methoxy substituted diazonium salts, it is possible to begin the synthesis with 2-nitro-anisidin. Up to an identical fundamental substance as results from the above synthesis, the steps of lactone condensation, reduction of the nitro group to the amine, and replacement of the amino group by a chlorine atom by means of Sandmeyer reaction are carried out. Furthermore, it is possible to produce the diazonium salt starting from o-chloro-p-nitrophenol. Here the phenol is alkylated in a first step and then reduced to the amine. However, because of the strong minus M effect of the nitro group, the alkylation of p-nitrophenols usually proceeds unsatisfactorily.

The synthesis of the compounds listed in the following table will be described below.

The listed compounds in the Table have the moiety expressed in the preceding compound unless a different moiety is indicated, e.g., compound 5 has a methylphenylthio group for $R_1$, a methyl group for $R_2$ and for $R_4$, and a hydrogen atom for $R_3$.

TABLE ($R_5$ to $R_8$ = H)

| Compound No. | $R_1$ | $R_2$ | $R_3$ | $R_4$ | $R_9$ | m.p. (°C.) | UV spectrum[1] (nm) |
|---|---|---|---|---|---|---|---|
| 1 | Cl | CH$_3$ | H | CH$_3$ | H | 61 | |
| 2 | | | | | NO$_2$ | 150–151 | |
| 3 | | | | | NO$_2$ | 187–188 | |
| | CH$_3$—〇—S | | | | | | |
| 4 | | | | | NH$_2$ | 196 | |
| 5 | | | | | N$_2^\oplus$ | | 368/408s |
| 6 | CH$_3$(CH$_2$)$_3$—S | | | | NO$_2$ | 113 | |
| 7 | | | | | NH$_2$ | 154 | |
| 8 | | | | | N$_2^\oplus$ | | 378/405s |
| 9 | | | | | NO$_2$ | 156 | |
| | 〇—S | | | | | | |
| 10 | | | | | NH$_2$ | 142 | |
| 11 | | | | | N$_2^\oplus$ | | 368/405s |
| 12 | | | | | NO$_2$ | 147 | |
| | 〇—CH$_2$—S | | | | | | |
| 13 | | | | | NH$_2$ | oil | |
| 14 | | | | | N$_2^\oplus$ | | 370/405s |
| 15 | Cl | C$_2$H$_5$ | | | H | oil | |
| 16 | | | | | NO$_2$ | 119–121 | |
| 17 | | | | | NO$_2$ | 141 | |
| | H$_3$C—〇—S | | | | | | |
| 18 | | | | | NH$_2$ | 102 | |
| 19 | | | | | N$_2^\oplus$ | | 370/410 |
| 20 | Cl | CH$_2$CH$_2$—OCH$_3$ | | | H | oil | |
| 21 | | | | | NO$_2$ | oil | |
| 22 | | | | | | 176 | |
| | H$_3$C—〇—S | | | | | | |
| 23 | | | | | NH$_2$ | 94 | |
| 24 | | | | | N$_2^\oplus$ | | 370/408s |
| 25 | Cl | —〇—Cl | | | H | oil | |
| 26 | | | | | NO$_2$ | 140 | |
| 27 | | | | | | 183 | |
| | H$_3$C—〇—S | | | | | | |
| 28 | | | | | NH$_2$ | 142 | |
| 29 | | | | | N$_2^\oplus$ | | 375/400s |
| 30 | | CH$_3$ | | (CH$_2$)$_6$CH$_3$ | N$_2^\oplus$ | | |
| 31 | | | | (CH$_2$)$_4$CH$_3$ | N$_2^\oplus$ | | |
| 32 | | C$_4$H$_9$ | | C$_2$H$_5$ | N$_2^\oplus$ $R_8$ = CH$_3$ | | |

[1]The maxima of the diazonium salts were determined in the sensitized layers of Example III below. The salts utilized are the zinc chloride double salts.

PROCESSES FOR PREPARING COMPOUNDS NOS. 1–5

(a) Compound No. 1

660 g. of 3-chloro-4-methoxyaniline (4.19 mol) is reacted with 3 ml. of concentrated sulfuric acid, 500 ml. of o-xylol, and 462 g. of γ-valerolactone (4.19 mol). The solution is refluxed for 6 hours, the water formed being distilled off azeotropically. At the end of the reaction, the xylol is removed by distillation and washed neutral with 3 lots of 100 ml. of water. Recrystallization from methanol gives a white powder having an m.p. of 61.° C. The yield of substantially pure raw product is 1107 g. or 95% of the theoretical.

(b) Compound No. 2

210 g. of compound No. 1 (0.876 mol) is dissolved in 420 ml. of glacial acetic acid and slowly added dropwise to a mixture of 130 ml. of $HNO_3$ (65%) and 630 ml. of glacial acetic acid at 100° C. Thereafter stirring is continued for 3 hours, and the mixture is poured when cool in 5 liters of ice water. The nitro compound precipitates out in the form of brownish-yellow crystals. Recrystallization from methanol yields 224 g. or 90% of the theoretical. m.p. 151° C.

(c) Compound No. 3

96 g. of thiocresol (0.77 mol) is dissolved together with 50 g. of potassium hydroxide in dimethyl formamide. At 20° C., 212 g. of compound No. 2 (0.745 mol) is added in portions, and the reaction temperature is gradually increased to 160° C. After 3 hours the reaction is ended. After cooling, the mixture is poured in 2 liters of ice water and filtered off the crystals. The product recrystallized from ethyl acetate has an m.p. of 190° C. The yield of pure product is 236 g. or 85% of the theoretical.

(d) Compound No. 4

225 g. of compound No. 3 (0.68 mol) is dissolved with stirring in 10200 ml. of benzene and heated to reflux. 2550 g. of freshly activated FeO (powder) is added all at once. At reflux, 0.5–1 ml. of water is added per hour, depending upon the course of the reaction, which is ended after 5–6 hours. The hot mixture is filtered over kieselguhr and washed 5 times with 500 ml. of benzene. After concentration, the product is recrystallized from 5 liters of methanol. Yield 196 g. (83.66%), m.p. 196° C. The method is described in Houben-Weyl, Vol. II/I, pp. 398–399. Well-known reduction processes, e.g., according to Bechamp or by means of catalytic hydrogenation, may equally well be used.

(e) Compound No. 5

10.4 g. of compound No. 4 (0.03 mol) is dissolved in 100 ml. of acetone and reacted at 0° C. with 25 ml. of 32% hydrochloric acid. At the same temperature, 20 ml. of 2 N sodium nitrite solution is slowly added. After diazotation has ended, the mixture is reacted with 9 ml. of 50% zinc chloride solution, and the acetone is evaporated in vacuo at room temperature. Yellow crystals of the zinc chloride double salt are precipitated. Yield after drying is 13.3 g. or 90% of the theoretical.

In a corresponding manner as described above, compounds Nos. 6–29 of the foregoing table may be prepared with good yields by fundamentally analogous methods.

As already mentioned, the compounds according to this invention may be used as light-sensitive components in diazotype materials. The latter may, for example, be so-called one-component diazotype material developed with a liquid developer, so-called two-component diazotype material developed by gaseous ammonia, or diazotype material to be developed through the application of heat. The preferred use is for the manufacture of one-component material, it being possible to use any desired carrier, which may, in particular, be either opaque or transparent, such as paper, linen, cardboard, metal foil, pigmented organic film or transparent paper, or transparent organic films such as polypropylene, polyester, cellulose ester, and others.

If the diazotype material according to the present invention is a two-component material, it is preferable to use weakly active couplers such as 2-hydroxy-biguanidinonaphthalene or 3,6-disulfo-2-hydroxynaphthalene. As thermal diazo material, one such as is described in U.K. Pat. Nos. 815,005 and 983,799 is produced.

A master may be produced by using grained aluminum or a diazo paper specially suited to the purpose, e.g., baryte-coated paper of the quality available under the trade name "Dryphoto mat" from Papeteries Steinbach & Cie., Malmedy, Belgium, or diazo coating cardboard as available from Papierfabrik Cham, Switzerland. The material is sensitized from an aqueous or organic-aqueous solution in a manner known per se. This solution may additionally contain stabilizers, such as citric acid, tartaric acid, boric acid, benzene sulfonic acid or naphthalene sulfonic acid or salts thereof, metallic salts, e.g., zinc chloride, magnesium chloride, nickel sulfate, and alum. According to the invention, it is also possible to use surface-finishing agents such as colloidal or non-colloidal silica, alumina, rice starch, barium sulfate, and others; binders such as gum arabic, gelatin, cellulose ethers, starch derivatives, polyvinyl alcohols, polyacrylic acids, polymaleic acids and copolymers thereof; and dispersions of organic plastic for for building up the material.

Furthermore, films having a flat gradation can be produced by using the thin-film technique or by the application of UV absorbers.

Particularly suitable compounds are such as have a benzamido or an S-alkyl, S-aralkyl, or S-aryl group in para position to the diazo group. Such compounds are notable for high light sensitivity and coupling activity. The photodecomposition products are colorless, and the azo dyes formed exhibit very good light fastness.

The production of diazotype material according to this invention will now be described in detail with reference to the following examples.

Developers

Developers for one-component materials often vary in their composition. Fundamentally, however, they consist of a water-soluble organic buffer system containing coupling components, usually phloroglucinol, resorcinol, and acetanilide, as well as wetting agents and antioxidant agents. Weakly acid developers with organich acid-base pairs having pK values of 4–6.5 have become widely used in practice. The two developers specified below are used in the following examples:

Developer I is a solution of
  8 g. phloroglucinol
  0.1 g. acetanilide 0.3 g. "Pluriol 10800"(trade name for polyethylene oxide available from BASF, Ludwigshafen, West Germany)

8 g. thiourea 2.3 g. benzoic acid 15 g. sodium benzoate 130 g. sodium formate 1000 ml. water The pH of the solution is approximately 5.8.

Developer II is a solution of 6 g. phloroglucinol 4.5 g. resorcinol 0.4 g. 2-ethyl-1hexyl-sulfate (as available from Union Carbide Corporation under the trade name "Tergitol 08")

0.3 g. sodium bisulfite 15 g. sodium formate 20 g. disodium adipate 45 g. trisodium citrate.2H$_2$O 2 g. adipic acid 1000 ml. water The pH of the solution is approximately 6.4.

Instead of phloroglucinol or resorcinol, other coupling components such as 2,3-dihydroxynaphthalene or 2-hydroxynaphthalene may also be used in weakly acid developers.

For sensitizing the carrier materials, the following basic compositions may be used:

Solution A for opaque materials:
1-2% diazonium salt
10 g. citric acid
3 g. saponin
1000 ml. water Solution B for transparent materials:
5-7% diazonium salt
10 g. citric acid
3 g. saponin
100-200 ml. isopropanol or acetone
800-1000 ml. water.

Additional or other components may be used if these solutions, e.g., stabilizers, silicic acid, dispersions of plastics, etc.

The sensitized layers are produced by methods known per se, e.g., in the case of paper or film, the solution is applied by means of rollers, and the surplus liquid is blown off by an air knife. The solution is applied to the paper or film in an amount of about 10–16 ml/m$^2$. The layer is applied to aluminum plates or paper-base offset plates by the usual centrifugal technique.

EXAMPLE I

A diazo base paper is sensitized with solution A, containing 20 g. of compound No. 5 according to the invention as zinc chloride double salt (sample 1). An identical paper is sensitized with solution A containing 20 g. of 1-diazo-5-methoxy-2-pyrrolid-2-one-1-yl-4-p-tolylthiobenzene zinc chloride double salt as a known comparative substance (sample 2).

The amount of solution applied to each of the papers is 16 ml. per m$^2$ of surface.

A 20-cm. wide strip of each paper is exposed over 10 cm. These samples are developed by dipping for 2 seconds in developer solution II. After drying, the sample 1 paper exhibits no haze of color in the exposed portion. Sample 2 exhibits a clearly perceivable haze of color brought about by so-called bleeding. Both samples show similar reddish-brown hues. Exposure through a Kodak-20 gradated wedge ($\alpha OD = 0.15$) shows that the sample 1 paper is somewhat faster than that of sample 2.

EXAMPLE II

Similarly goods results were obtained in a comparison of compounds 8, 11, and 29 of the present invention with prior art compounds as follows:

Compound 8 compared with 1-diazo-5-methoxy-4-n-butylthio-2-pyrrolid-2-one-1-yl-benzene zinc chloride double salt and Compund 11 compared with 1-diazo-5-methoxy-4-phenylthio-2-pyrrolid-2-one-1-yl benzene zinc chloride double salt, or Compound 29 compared with 1-diazo-5-p-chlorophenoxy-2-pyrrolid-2-one-1-yl-benzene zinc chloride double salt.

EXAMPLE III

A transparent paper having a hydrophilic, polyvinylacetate-base coating is sensitized with 50 g. each of compounds 5, 8, 11, 14, 19, 24, and 29 in solution B, exposed through a Kodak-20 gradated wedge (as in Example I), and then developed with developer I. All compounds prove to yield approximately the same quality of reproduction. The azo dyes formed in the layer with phloroglucinol show the following absorption maxima in the electromagnetic absorption spectrum:

Compound No. 5—420/555 (nm)

Compound No. 8—405/545

Compound No. 11—415/546

Compound No. 14—465/550 s

Compound No. 19—410/562

Compound No. 24—416/562

Compound No. 29—408/534

A two-component diazotype material according to the invention can be produced by incorporating a compound of formula I in a layer known per se and coating the desired carrier material. The material according to this invention may also be provided with slow-coupling components, e.g., 7'-hydroxy-1',2',4,5-naphthimidazole or 2-hydroxy-8-biguanidino-naphthalene as is described in German Pat. No. 1,814,283.

What is claimed is:

1. Photosensitive benzene diazonium compound of the formula:

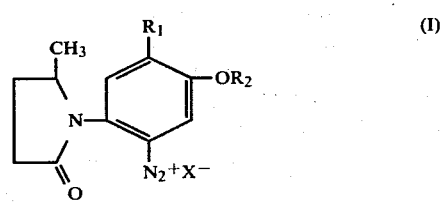

wherein R$_1$ is p-methylphenylthio; R$_2$ is methyl, and X is an anion.

2. A compound according to claim 1 of formula I, wherein X is a chlorine, tetrafluoroborate, hexafluorophosphate, or ½ZnCl$_4^-$ ion.

3. A compound according to claim 1 of formula I, wherein X is a ½ZnCl$_4^-$ ion.

4. A one-component diazotype material having a support containing thereon a photosensitive layer comprising a photosensitive benzene diazonium salt of the formula

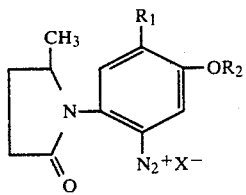 (I)

wherein R₁ is p-methylphenylthio; R₂ is methyl; and X is an anion.

5. A one-component diazotype material according to claim 4, having a support and containing thereon a photosensitive layer comprising a photosensitive benzene diazonium salt of the formula I, wherein X is a chlorine, tetrafluoroborate, hexafluorophosphate, or ½ZnCl₄⁻ ion.

6. A one-component diazotype material according to claim 4, having a support and containing thereon a photosensitive layer comprising a photosensitive benzene diazonium salt of the formula I, wherein X is a ½ZnCl₄⁻ ion.

* * * * *